(12) United States Patent  
Lavoie et al.

(10) Patent No.: US 9,389,201 B2  
(45) Date of Patent: Jul. 12, 2016

(54) ADAPTIVE ELECTROMAGNETIC PROBE FOR TWISTED TUBE HEAT EXCHANGER

(71) Applicant: EDDYFI NDT INC., Québec (CA)

(72) Inventors: Olivier Lavoie, Saint-Gabriel-de-Valcartier (CA); Martin Bourgault, Saint-Nicolas (CA); Marc Grenier, Québec (CA); François Dion, Québec (CA)

(73) Assignee: EddyFi NDT inc., Quebec (CA)

( * ) Notice: Subject to any disclaimer, the term of this patent is extended or adjusted under 35 U.S.C. 154(b) by 220 days.

(21) Appl. No.: 14/300,681

(22) Filed: Jun. 10, 2014

(65) Prior Publication Data

US 2014/0361764 A1    Dec. 11, 2014

Related U.S. Application Data

(60) Provisional application No. 61/833,686, filed on Jun. 11, 2013.

(51) Int. Cl.
*G01N 27/90* (2006.01)
*G01N 27/82* (2006.01)

(52) U.S. Cl.
CPC ............ *G01N 27/82* (2013.01); *G01N 27/9013* (2013.01)

(58) Field of Classification Search
CPC . G01N 27/82; G01N 27/9013; G01N 27/902; F28F 27/00; F25B 49/005; Y10S 165/008; Y10S 165/001

USPC ......... 324/219–221, 228–243; 73/623, 865.8; 165/11.1, 11.2, 76, 94, 95
See application file for complete search history.

(56) References Cited

U.S. PATENT DOCUMENTS

| | | | | |
|---|---|---|---|---|
| 5,247,251 | A * | 9/1993 | Yost | F22B 37/003 165/11.1 |
| 6,246,817 | B1 * | 6/2001 | Griffin | A61B 18/22 385/43 |
| 8,794,083 | B2 * | 8/2014 | Draper | F16L 55/30 104/138.2 |
| 2011/0089937 | A1 * | 4/2011 | Petrosky | G01N 27/90 324/220 |

* cited by examiner

*Primary Examiner* — Arleen M Vazquez
*Assistant Examiner* — Robert P Alejnikov, Jr.
(74) *Attorney, Agent, or Firm* — Fasken Martineau Dumoulin LLP (57) ABSTRACT

An electromagnetic probe for non-destructive inspection of a twisted tube of a twisted tube heat exchanger comprising a probe body having a sensing section being configured to allow circulation of the probe body within the length of circular tube and the length of helical oval tube and to allow displacement of the electromagnetic sensor(s) from a radially inward contracted position to a radially outward expanded position in close proximity to an interior surface of a crest of the oval tube; a conduit attached to a proximal end of the probe body, the at least one conductor extending within the conduit to a remote end of the electromagnetic probe.

14 Claims, 10 Drawing Sheets

ADAPTIVE ELECTROMAGNETIC PROBE FOR TWISTED TUBE HEAT EXCHANGER

TECHNICAL FIELD

The invention relates to non-destructive inspection of twisted tube heat exchangers and more specifically to an adaptive electromagnetic probe which adapts to the internal shape of the twisted tube.

BACKGROUND OF THE ART

Since 1985, a new design of heat exchangers with a new type of twisted tube configuration started to be installed worldwide under various field conditions. The main advantage of these twisted tube heat exchangers is their excellent heat transfer performance and smaller footprint (up to 30% smaller than conventional round tube heat exchanger). However, commonly used nondestructive inspection techniques are not able to perform a reliable and accurate inspection of the twisted tubes.

Currently, twisted tubes found in heat exchangers are being inspected with electromagnetic methods: Remote Field Testing (RFT) is used for all ferromagnetic material such as carbon steel, duplex steel and nickel, while Eddy Current Testing (ECT) is used for non-ferromagnetic material such as titanium, stainless steel, brass and copper-nickel. These two inspection techniques make use of cylindrical probes (featuring a circular cross-section). The largest cylindrical object that can be inserted, pushed and pulled freely in the twisted tubes determines the diameter of the aforementioned probes. Because of their very nature, electromagnetic methods work best when probes are closest to the surface being examined. The circular probes currently in use by the industry are therefore delivering sub-optimal performances: flaw detection, flaw characterization and sizing are often problematic due to poor signal-to-noise ratios.

These RFT and ECT probes are well known in the art but are not ideal to locate, characterize and assess defect size during the non-destructive examination of twisted heat exchanger tubing. Indeed, flaws located on the tube wall furthest away from the center (aka the crest) produce much smaller, distorted, signals than same-size flaws located in the narrow section closest to the tube center (aka the dip). This translates into a reduced probability of detection. The common sizing method for determining flaw depth is inaccurate because of the reduced sensitivity and the large tube signal variations coming from the various flaw locations (crest or dip).

Moreover, because the heat exchanger has a plurality of twisted tubes in close contact to one another, the inspection results are greatly affected by the presence of the adjacent tubes. Therefore, even if a conventional circular probe can detect some flaws in the crest (with a reduced sensitivity) when the tube is taken in isolation, the detection capability is reduced considerably when the same flaw is located in a tube bundle, under real-life conditions. This reduction in sensitivity is particularly important when using the RFT technique.

SUMMARY

According to one broad aspect of the present invention, there is provided an electromagnetic probe for non-destructive inspection of a twisted tube of a twisted tube heat exchanger, the twisted tube comprising at least one length of circular tube and a length of helical oval tube, the helical oval tube being an oval tube twisted into an helix. The probe comprising a probe body adapted to be inserted inside the twisted tube, the probe body having a sensing section provided at its distal end, the sensing section having at least one electromagnetic sensor connected to a respective at least one conductor provided within the probe body, the sensing section being configured to allow circulation of the probe body within the length of circular tube and the length of helical oval tube and to allow displacement of the at least one electromagnetic sensor from a radially inward contracted position to a radially outward expanded position in close proximity to an interior surface of a crest of the oval tube when the probe body is located in the length of helical oval tube, the close proximity being a distance smaller than a difference between a major axis and a minor axis of the helix; a conduit attached to a proximal end of the probe body, the at least one conductor extending within the conduit to a remote end of the electromagnetic probe.

In one embodiment, the sensing section comprises at least one outward biased protrusion biased to be in an expanded configuration, and being adapted to be movable to an inward contracted configuration upon external pressure from the interior surface of the twisted tube.

In one embodiment, the at least one outward biased protrusion is two opposed outward biased protrusions.

In one embodiment, each outward biased protrusion is one of a flexible arm, a compressible flange, a resilient flange, a spring-loaded flange and an outwardly biased flange.

In one embodiment, the probe body has a probe head portion and a probe tail portion, the probe head and the probe tail portions being in rotational interconnection, the sensing section being provided on the probe head portion.

In one embodiment, the probe further comprises at least one additional electromagnetic sensor on the probe tail portion of the probe body.

In one embodiment, the rotational interconnection is a contact slip ring.

In one embodiment, the probe tail portion has a circular cross section with a diameter maximized for displacement in the length of oval tube.

In one embodiment, the probe further comprises at least one supplemental sensing section, the at least one supplemental sensing section being in at least one of rigid, angular and rotational interconnection with the sensing section, the supplemental sensing section having at least one supplemental electromagnetic sensor.

In one embodiment, the supplemental sensing section is a helically shaped sensing section, a configuration of the helically shaped sensing section being adapted to match at least a portion of a pitch of the helix of the twisted tube.

In one embodiment, the probe further comprises a spatial angular sensing device for determining an angular position of the at least one electromagnetic sensor in the twisted tube.

In one embodiment, each electromagnetic sensor is chosen among the group consisting of a RFT emitter, a RFT receiver, an Eddy current emitter, an Eddy current receiver and an Eddy current combined emitter-receiver.

In one embodiment, the electromagnetic sensor is one of a coil, a Hall effect sensor and a Giant Magneto-resistive sensor and if the electromagnetic sensor is a coil, the coil is one of a circular pancake coil, an oval pancake coil, a circumferential coil and an orthogonal coil.

In one embodiment, the at least one electromagnetic sensor is an array of electromagnetic sensors.

In one embodiment, the sensing section comprises an expandable chamber, the at least one electromagnetic sensor being provided on a wall of the expandable chamber, the expandable chamber being adapted to receive a filler to expand and to be emptied to contract, the filler being at least one of air, gas, liquid, aqueous liquid, viscous material, the wall being made of a flexible material.

BRIEF DESCRIPTION OF THE DRAWINGS

Having thus generally described the nature of the invention, reference will now be made to the accompanying drawings, showing by way of illustration example embodiments thereof and in which:

FIG. 2 includes FIG. 2A and FIG. 2B which show cross-section views of the twisted section of the tube, FIG. 2A showing the maximum diameter of a prior art circular cross-section probe which fits inside the twisted tube and the overall tube footprint

FIG. 5 includes FIG. 5A and FIG. 5B which show an example electromagnetic sensor arrangement for the ECT inspection technique with an adaptive probe assembly of the type of FIG. 4, FIG. 5B being a rotated version of FIG. 5A;

FIG. 6 includes FIG. 6A and FIG. 6B which show an example electromagnetic sensor arrangement for the RFT inspection technique with an adaptive probe assembly of the type of FIG. 4, FIG. 6B being a rotated version of FIG. 6A;

FIG. 8 includes FIG. 8A and FIG. 8B which show another example embodiment of an adaptive probe assembly with two outward biased protrusions which are resilient flanges, FIG. 8B being a rotated version of FIG. 8A;

FIG. 9 includes FIG. 9A an FIG. 9B in which FIG. 9A shows the probe of FIG. 8A in an inward contracted configuration and FIG. 9B shows a cross-section view of the head portion of the probe of FIG. 8A; and FIG. 10 includes FIG. 10A and FIG. 10B which show another example embodiment of an adaptive probe assembly with two contractible modules and a spacer element between the probe head and the probe body, FIG. 10B being a rotated version of FIG. 10A.

It will be noted that throughout the appended drawings, like features are identified by like reference numerals.

DETAILED DESCRIPTION

Figure 1:
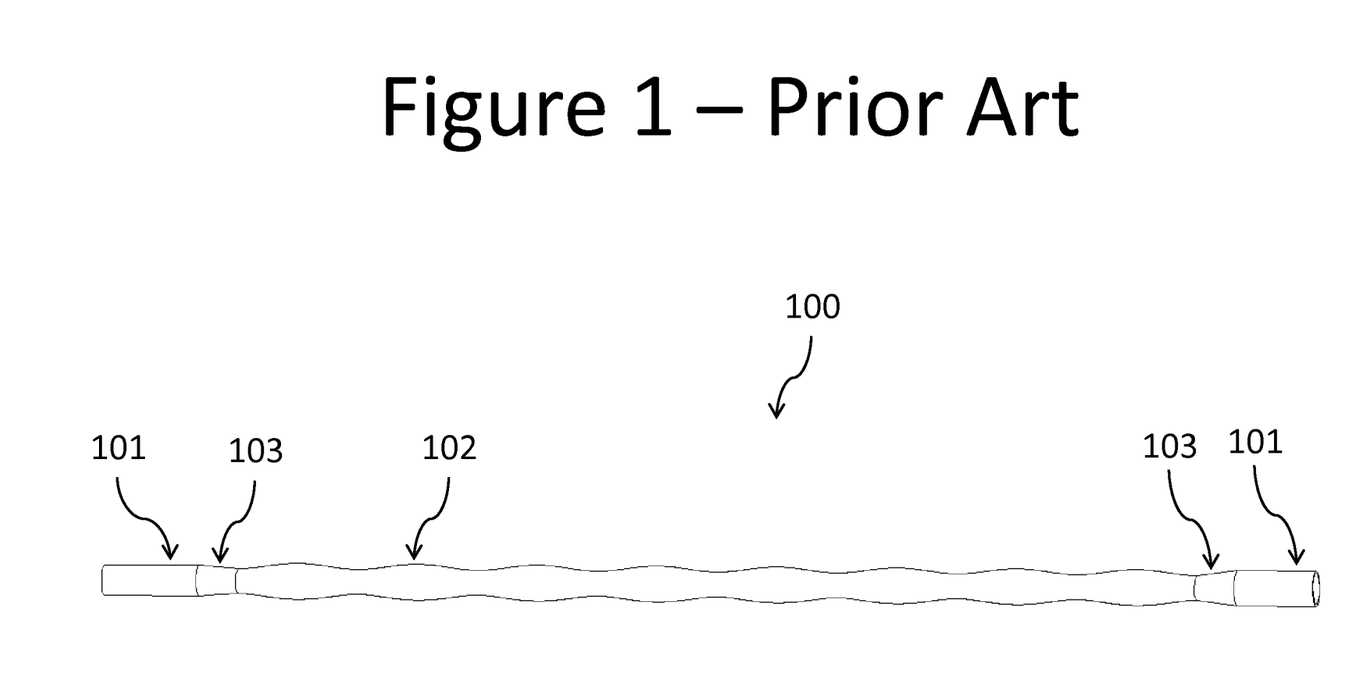
FIG. 1 shows a typical twisted tube used in some heat exchanger designs.

FIG. 1 illustrates a typical twisted tube 100. At both ends 101, the tube is cylindrical with a circular cross section. In between, the tube has a twisted, elliptical shape 102. The twisted, elliptical shape can be thought of as a length of oval tube twisted into an helix with a constant or varying pitch, creating a helical oval tube. Typically, the helix will have a constant pitch but a number of different pitches are used in the art. A tapered section 103 ensures a transition between the helical oval tube section and the circular tube ends.

Figure 2A:
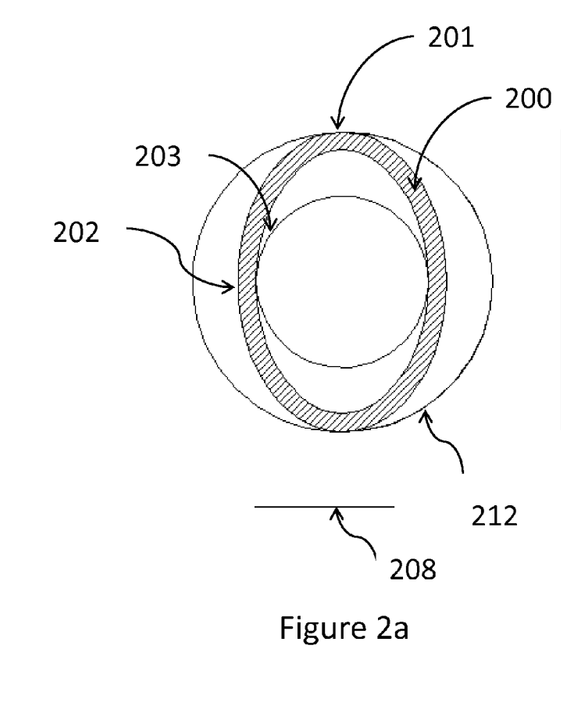
Figure 2B:
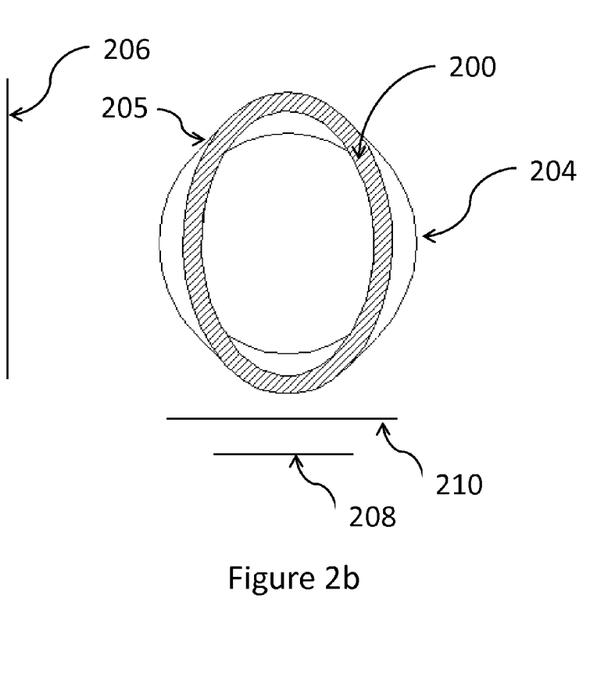
FIG. 2B shows the diameter of the circular tube ends.

FIG. 2 shows a cross-sectional view of the twisted section of the tube 200. The oval or ellipse portion of the tube has a major axis 206 (determining the crest 201) and a minor axis 208 (determining the dip 202), which are set at about 90 degrees to one another. The overall footprint 212 of the helical oval tube is shown in FIG. 2A and corresponds to a circle of a diameter equivalent to the major axis. As shown in FIG. 2B, the diameter 210 of both tube ends 204, which have a circular cross-section, is typically larger than the minor axis 208 and smaller than the major axis 206 of the helical oval tube. The tapered section 103 creates a region of varying diameter 205.

FIG. 2A shows the maximum size of a prior art circular probe 203 that may fit inside the tube 200. The maximum diameter of this prior art circular probe 203 is comparable to the minor axis 208. The circular probe 203 wall is very close to the interior tube wall at the dip 202. However, one can observe the large distance between the circular probe 203 wall and the interior tube wall at the crest 201. This large distance adversely affects the sensor's sensitivity and response, which reduces the probability of detecting flaws and the corresponding sizing accuracy.

Figure 3:
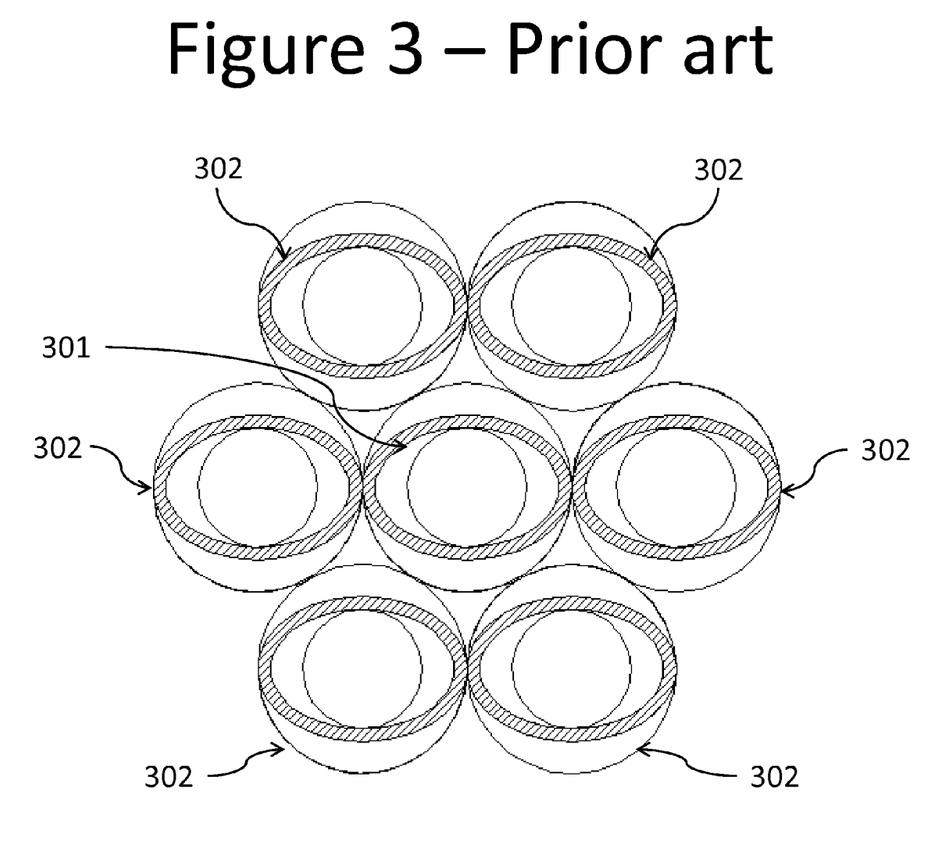
FIG. 3 shows a typical cross-section view of a bundle assembly for the twisted tubes in the heat exchanger.

FIG. 3 illustrates a typical bundle assembly of twisted tubes in the heat exchanger. In this type of arrangement, a central tube 301 is firmly supported by six surrounding tubes 302. Twisted tubes are therefore in contact with one another. This affects the electromagnetic environment seen by the probe considerably.

Figure 4:
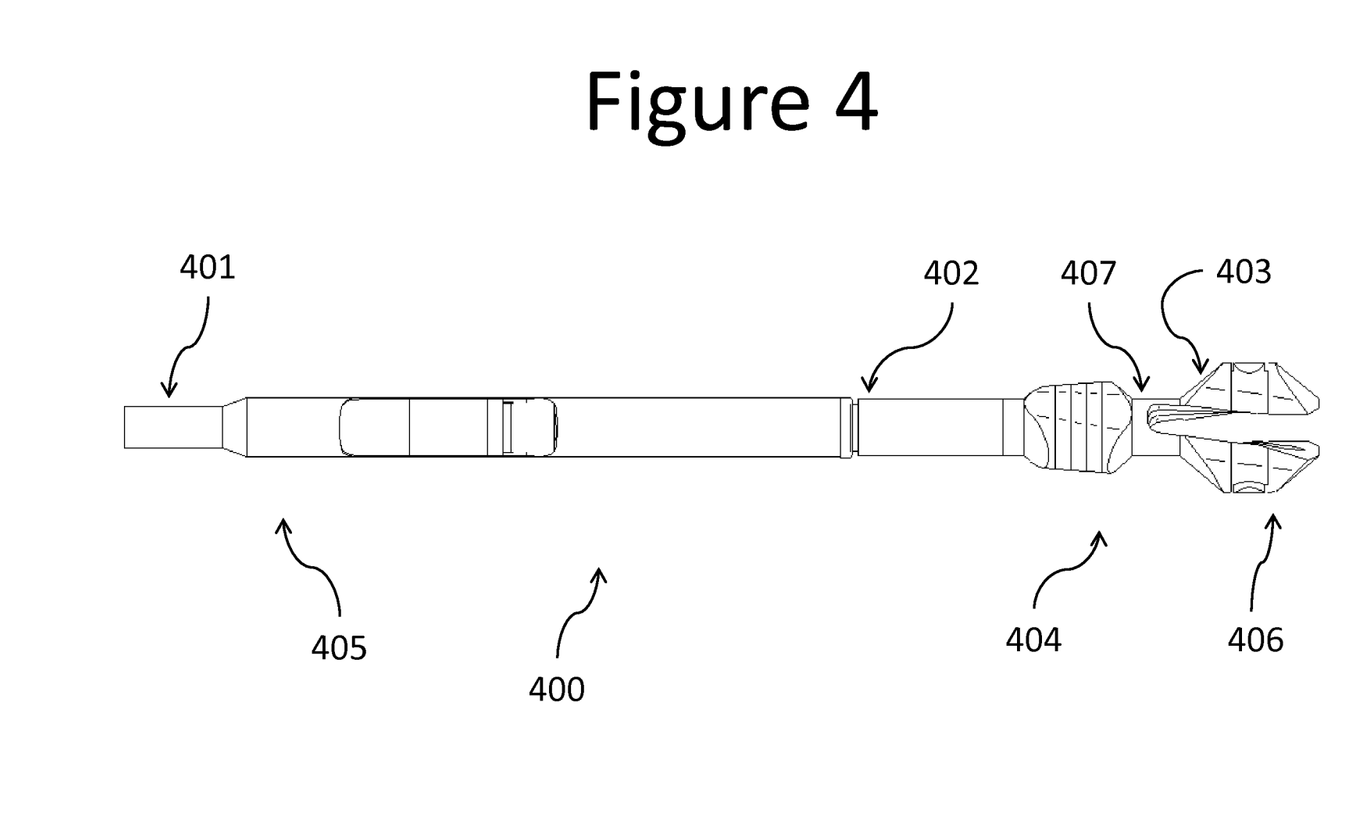
FIG. 4 shows an example embodiment of an adaptive probe assembly with two outward biased protrusions which are two opposed flexible arms.

FIG. 4 illustrates an example embodiment of the invention. The design allows the probe to be in close proximity and/or contact with the inside surface of the twisted tube. The probe 400 has a conduit 401 which extends from the probe body to remote electronic equipment. This conduit 401 is sufficiently long to allow insertion of the probe within the twisted tube and displacement of the probe within a length of the twisted tube. In most applications, the probe will be displaced from one end of the twisted tube to the other end. The displacement of the probe within the twisted tube may be done manually by an operator and/or using motorized methods. The conduit 401 houses the electrical conductors which extend from the electromagnetic sensor(s) provided in the probe to the remote electronic equipment.

In this embodiment, the probe assembly includes a slip ring 402 allowing a section of the probe to rotate as the probe is pushed or pulled in the twisted tube.

The probe head 403, at the extremity of the probe assembly 400, is self-adapting, in a resilient fashion, when being displaced in a twisted tube. This allows entry of the probe assembly in the circular section of the twisted tube where the diameter of the twisted tube is smaller than the major axis of helical oval section and further allows deployment of the probe head in the helical section to bring the electromagnetic sensor(s) as close as possible to the interior surface of the twisted tube.

The electromagnetic probe for non-destructive inspection of a twisted tube therefore comprises a probe body 400 adapted to be inserted inside the twisted tube. The probe body has an sensing section 403 at its distal end. The sensing section 403 has at least one electromagnetic sensor each connected to a conductor (not shown) provided within the probe body. The sensing section 403 is configured to contract to allow circulation of the probe body within the length of circular tube and the length of helical oval tube and to expand to bring the electromagnetic sensor(s) in close proximity to an interior surface of crests of the oval tube when the probe body is located in the length of helical oval tube. The shape of the sensing section 403 is modifiable according to a shape of the interior surface of the twisted tube. The electromagnetic probe also includes a conduit 401 attached to a proximal end of the probe body, the conductors extending within the conduit to a remote end of the electromagnetic probe. The sensing section 403 comprises a contractible head having at least one outward biased protrusion.

Once inserted in the helical portion of the twisted tube, the sensor is in close proximity to an interior surface of a crest of the oval tube. In this context, the close proximity is a distance smaller than a difference between a major axis and a minor axis of the helix. What this means is that the sensor is positioned radially outward of the interior diameter at the minor axis.

In the example shown in FIG. 4, the probe body has a probe head portion 404 and a probe tail portion 405. The probe head 404 and the probe tail 405 portions are in rotational interconnection. The sensing section 403 is provided on the probe head portion 404. In this example, the rotational interconnection is a contact slip ring 402.

In one embodiment, the probe head 404 is an elliptical shaped element. The major axis of the elliptical shape element is small enough to enter in the circular diameter section of the twisted tube.

The probe assembly may optionally include a spatial angular sensing device (not shown) providing information about a detected indication's location along the twisted tube.

In FIG. 4, two outward biased protrusions are shown. The outward biased protrusion(s) are biased to be in an expanded configuration and are adapted to be movable to an inward contracted configuration upon external pressure from the interior surface of the twisted tube.

Figure 7:
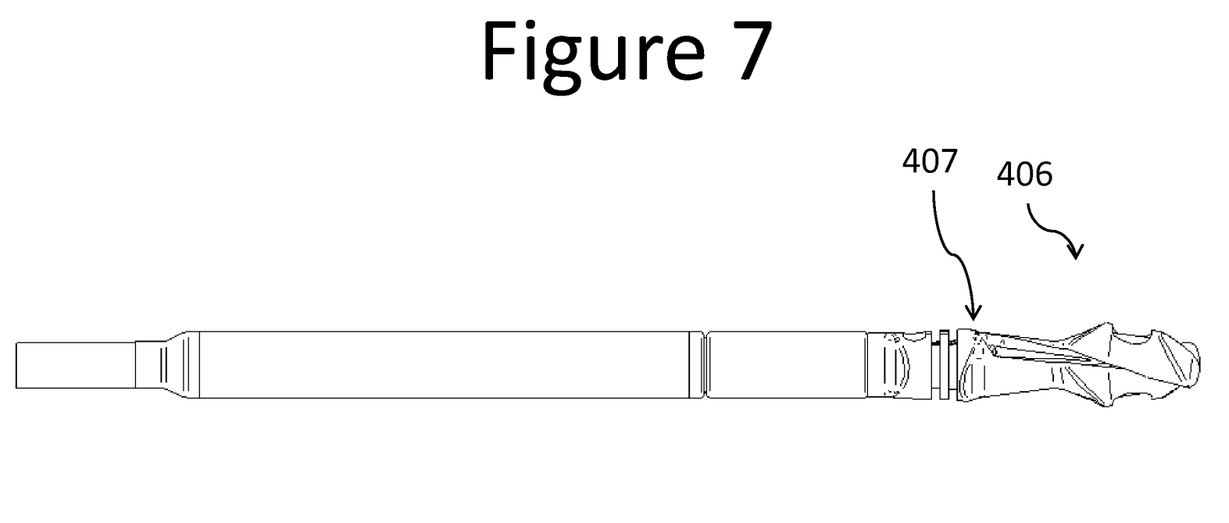
FIG. 7 shows another example embodiment of an adaptive probe assembly with two opposed flexible arms in an inward contracted configuration.

In the example shown in FIG. 4, the outward biased protrusion(s) are two opposed resilient arms 406 extending from a neck portion 407. The resilient arms 406 are adapted to each be pushed inwardly by the interior surface of the circular tube. As shown in FIG. 7, their interior surfaces may touch in the inward contracted configuration. This change in the angle of the longitudinal axis of each arm with respect to the longitudinal axis of the probe is made possible by a relative flexibility of the material of neck portion 407. As will be readily understood, the shape and positioning of the arms 406 and of neck portion 407 could be designed to create any number of different contracted configurations, one of which is shown in FIG. 7.

Alternatively, the outward biased protrusion(s) could be compressible flanges made of compressible material. Rigid resilient or spring-loaded flanges made of a rigid material but being provided in a resilient arrangement to allow movement, for example via a neck portion or a compressible seat made of a resilient material could also be used. The protrusions could also be flanges biased outwardly by any other means.

Figures 8, 8A, 8B:
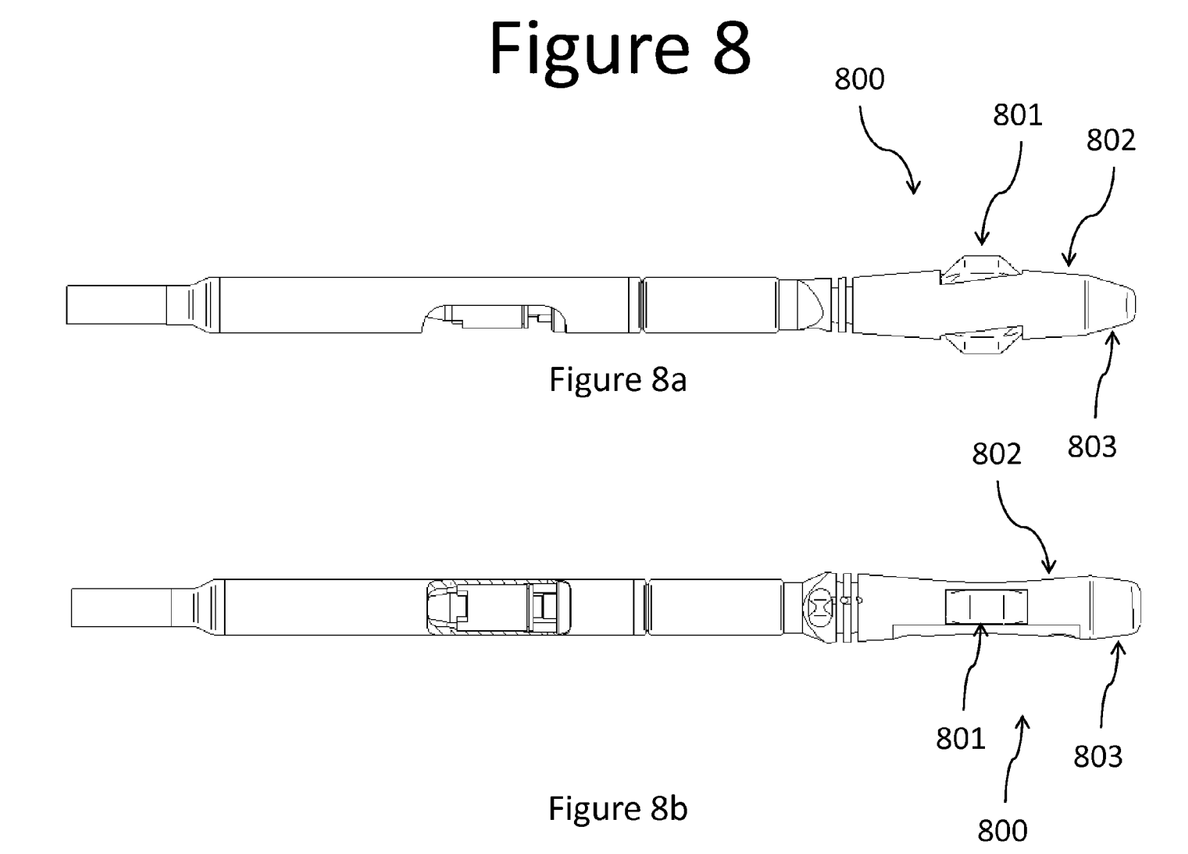

Such an alternative embodiment is shown in FIG. 8. The sensing section 800 comprises two contractible modules 801 biased to be in an expanded configuration and adapted to be movable to an inward contracted configuration shown in FIG. 9A upon external pressure from the interior surface of the twisted tube. The contractible modules 801 are rigid flanges provided in a foam seat which is itself compressible.

Figures 9, 9A, 9B:
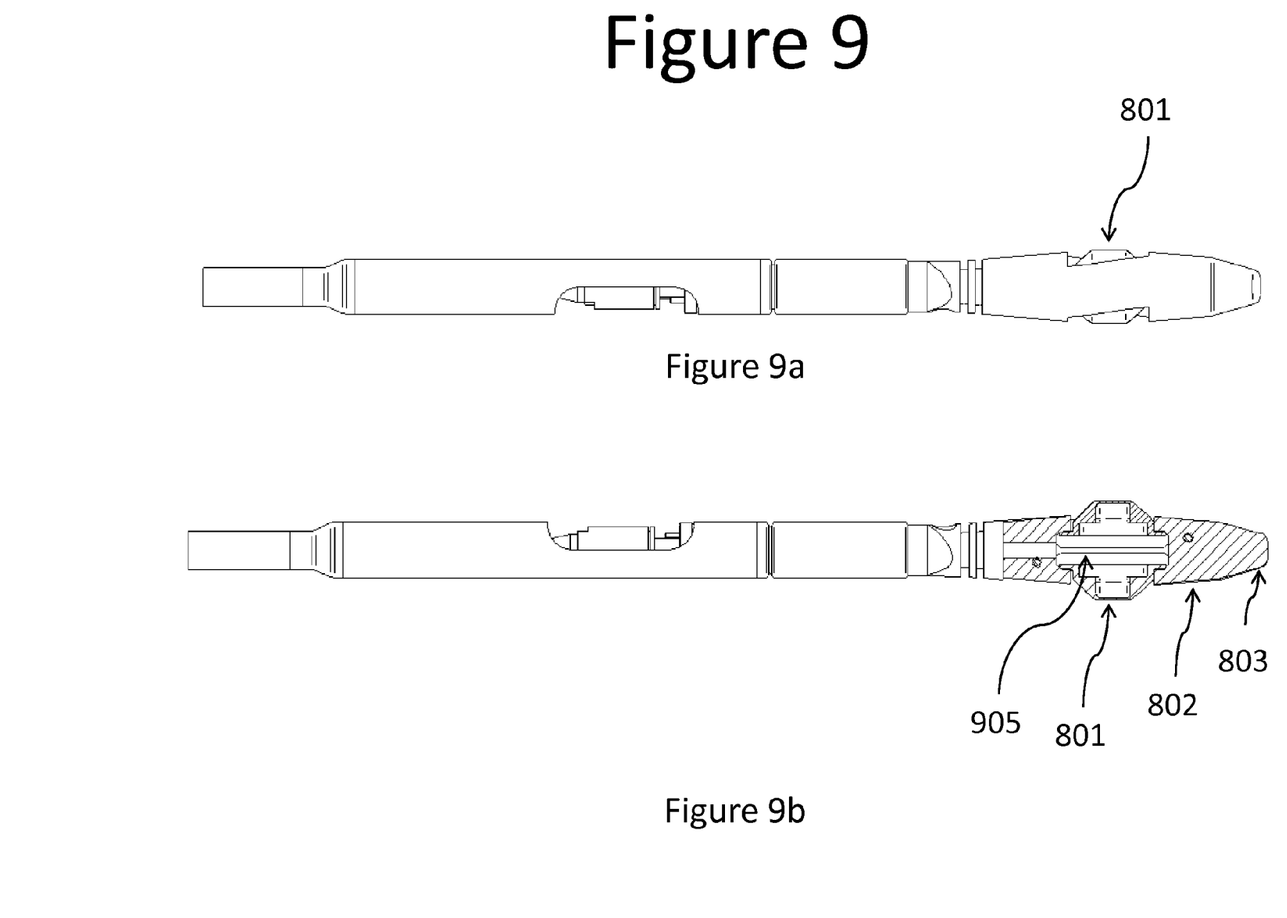

Shown in FIG. 9B is one example configuration for outwardly biasing the contractible modules 801 which uses compressible foam 905 inside the probe head housing 802. The compressible foam 905 material, density, thickness and mechanical configuration are chosen by the person skilled in the art so as to allow displacement of the contractible modules 801 from the outward extended position to the inward contracted configuration by an adequate distance for the twisted tube in which the probe is to be inserted.

In still another example embodiment (not shown), the sensing section comprises an expandable chamber. The electromagnetic sensor(s) being provided on a wall of the expandable chamber. The expandable chamber is adapted to receive a filler to expand (and/or inflate) and to be emptied to contract. The filler can be, for example, air, gas, liquid, aqueous liquid, viscous material. The wall can be made of a flexible material. In this embodiment, the probe head is contracted (emptied) for the insertion in the circular portion of the tube and then expanded (inflated) for the inspection of the helical portion. It is contracted (emptied) for withdrawal from the helical portion. The probe can therefore be considered to comprise a contractible head.

Another example embodiment of a contractible head for the probe (not shown) is a compressible helically shaped sensing section. A configuration of the compressible helically shaped sensing section is adapted to match at least a portion of the pitch of the helix of the twisted tube in the expanded configuration and to be compressed to circulate within the circular tube. The compressible helically shaped sensing section.

The electromagnetic sensor provided on the sensing section may be, for example, a RFT emitter, a RFT receiver, an Eddy current emitter, an Eddy current receiver or an Eddy current combined emitter-receiver. The electromagnetic sensor may be, for example, a coil, a Hall effect sensor or a Giant Magneto-resistive sensor. If the electromagnetic sensor is a coil, the coil may be, for example, a circular pancake coil, an oval pancake coil, a circumferential coil or an orthogonal coil. The coil can be arranged in a coil array.

In an alternative embodiment (not shown), the sensing section is a compressible helically shaped sensing section, a configuration of the compressible helically shaped sensing section being adapted to match the helix of the twisted tube. The material of the compressible helically shaped sensing section allowing to contract the sensing section for circulation in the circular tube and to bring the sensor(s) in close proximity to the crest in the helical tube.

Figures 5, 5A:
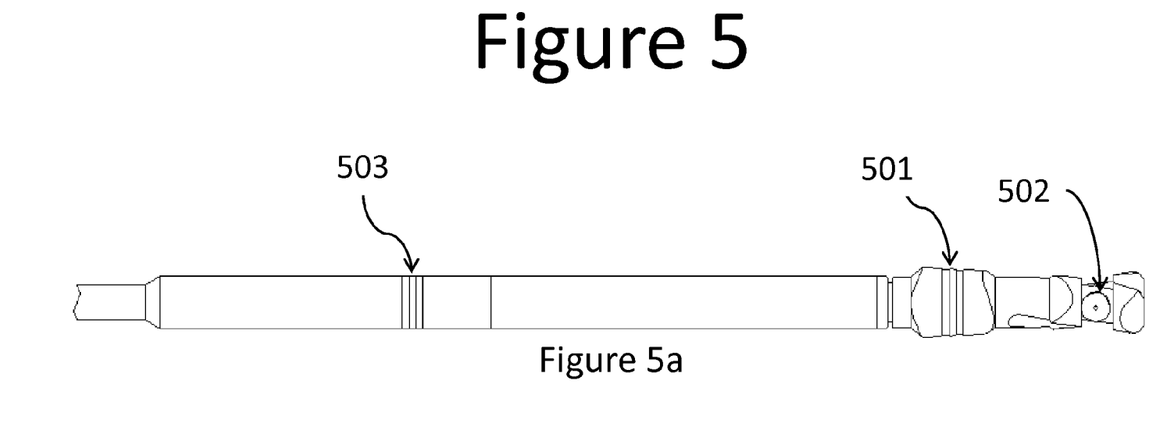
Figure 5B:
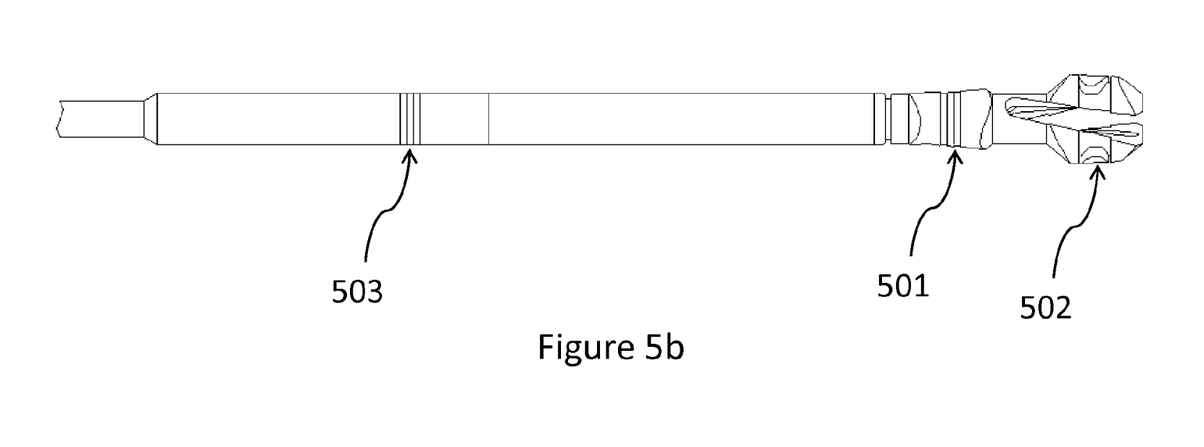

FIG. 5 illustrates an example electromagnetic sensor arrangement using the ECT inspection technique. The sensing section 502 comprises two outward biased protrusions. One or several surface coils arranged parallel to the surface (i.e their axes are perpendicular to the plane of the surface of the material) on the top of the self-adaptive twisted extremity of the sensing section 502. The surface coils can be used in absolute bridge mode to be sensitive to all defect orientation or in transmit-receive mode (if more than one coil is present on each arm) to offer a preferred sensitivity to a specific defect orientation. In both cases, the coils on the self-adaptive extremity are used to improve detection and sizing of the flaws and to confirm their location in the crest.

The example of FIG. 5 further comprises at least one supplemental sensing section. The supplemental sensing section can be in rigid, angular and/or rotational interconnection with the sensing section. The supplemental sensing section has at least one electromagnetic sensor. The supplemental sensing section is a helically shaped sensing section 501. The configuration of the helically shaped sensing section 501 is adapted to match the helix of the twisted tube. A twisted bobbin probe is provided on the supplemental sensing section 501 with the maximum dimension allowed by the tube internal diameter (in the circular section), to optimize general sensitivity in the twisted area by having a larger fill factor than smaller circular coil.

In the example of FIG. 5, the probe includes at least one additional electromagnetic sensor 503 on the probe tail portion of the probe body. In this example, the probe tail portion has a circular cross section with a diameter maximized for displacement in the oval tube. A standard bobbin probe is provided as the additional electromagnetic sensor 503 on the probe body to inspect the circular sections at both tube ends.

Figures 6, 6A, 6B:
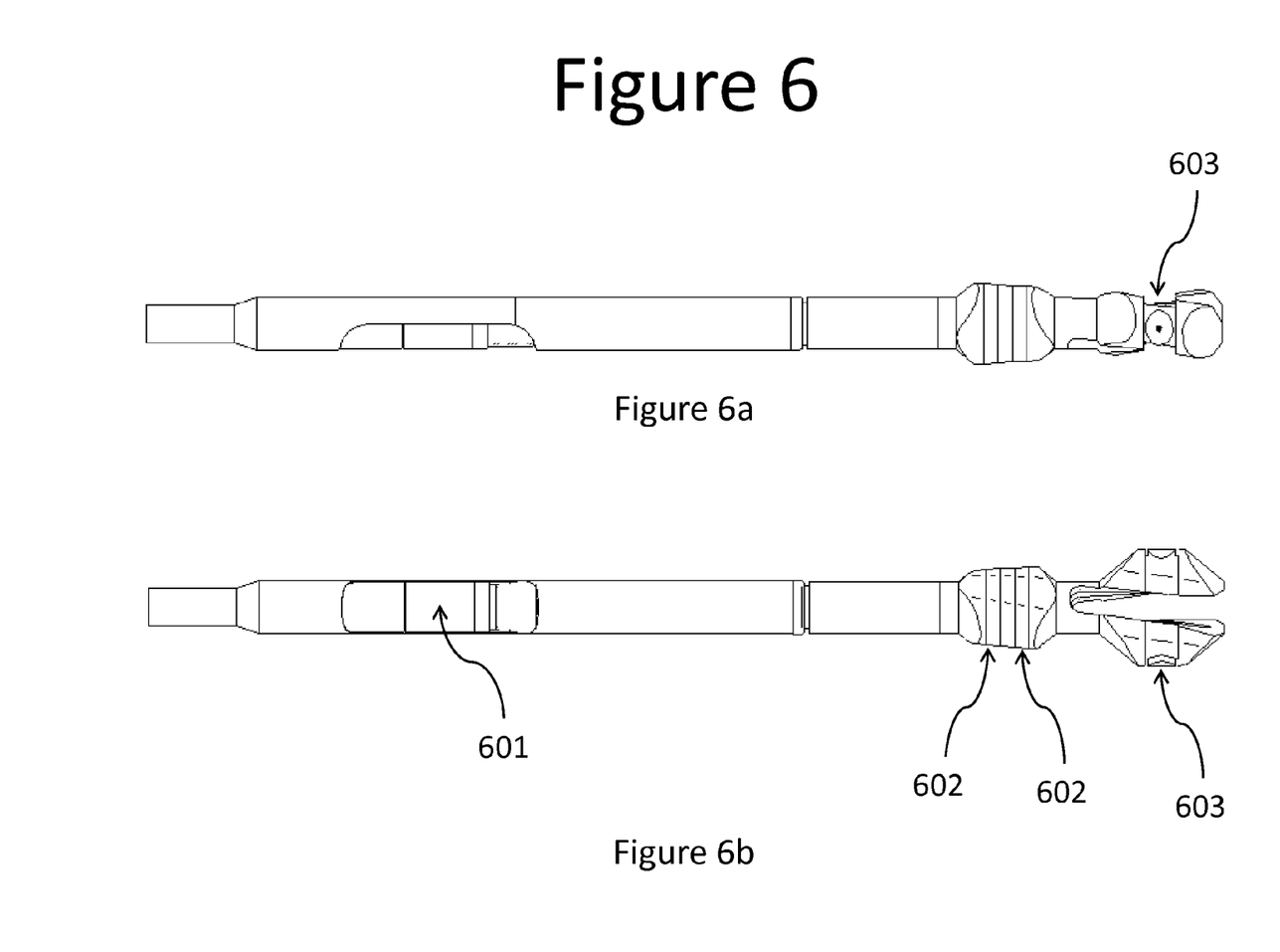

FIG. 6 illustrates an example electromagnetic sensor arrangement for the RFT inspection technique. One or several surface coils arranged parallel to the surface (i.e their axes are perpendicular to the plane of the surface of the material) on the top of the twisted extremity of the sensing section 603, to improve the detection and sizing of the flaws and to confirm their location in the crest.

The supplemental sensing section is a helically shaped sensing section 602. The configuration of the helically shaped sensing section 602 is adapted to match the helix of the twisted tube. A twisted receiver coils set is provided on the helically shaped sensing section 602. It has the maximum dimension allowed by the tube internal diameter (in the circular section), to optimize general sensitivity in the twisted area by having a larger fill factor than smaller circular coil.

An excitation coil is provided as the additional electromagnetic sensor 601 on the probe body. It is shown on the probe tail but could be located on the probe head to generate the low frequency remote field signal.

Figures 10, 10A:
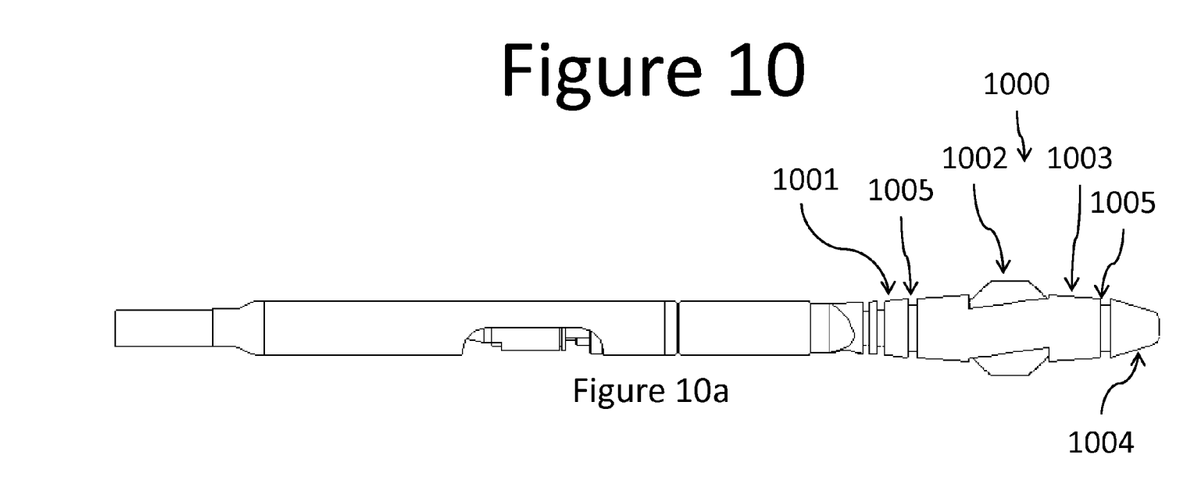
Figure 10B:
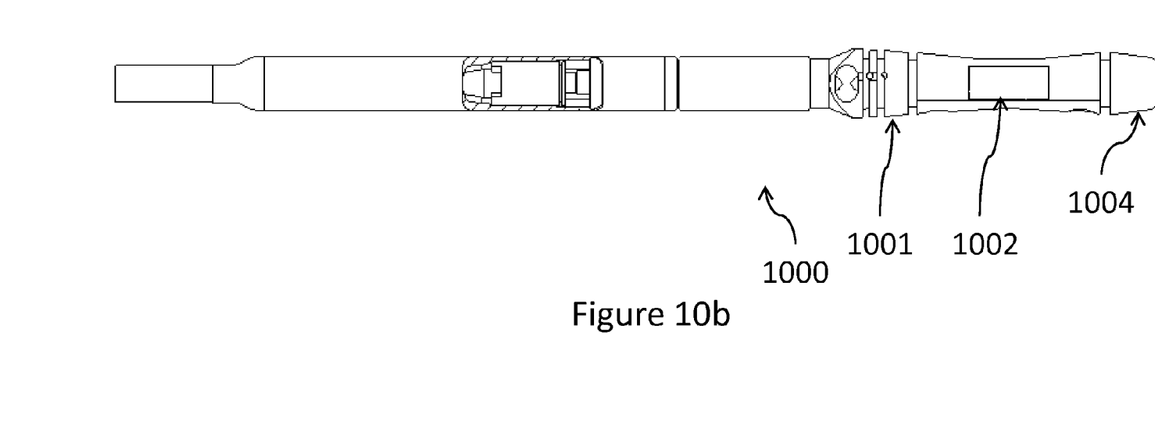

As will be readily understood, one may wish to create a probe body which can circulate in twisted tubes having different pitch angles. FIG. 10 shows an example probe housing which is divided in three sections 1001, 1003 and 1004 linked by two adjustable joints 1005. The adjustable joints 1005 are used to modify the angle between two sections in order to allow the probe assembly to move freely in twisted tubes having different pitch angle. The sensing section 1002 is located in the middle section 1003 of the probe assembly 1000.

In short, the configuration of the electromagnetic probe allows sensors to be in close contact with the inside surface of the twisted tubes of exchanger tubes (i.e. elliptical cross-section) during nondestructive examination. In use, the outward biased protrusion, when in the expanded configuration, is oriented in the direction of the major axis of the twisted tube. The outward biased protrusion is in contact with or close to the interior surface of the twisted tube. Compression of the protrusion into the contracted configuration reduces the cross section or overall footprint of the probe head section.

As will be readily understood, the helical oval tube of the twisted tube need not be a strict oval shape tube and may have any oval-type shape tube suitable for the application. It may be obround, ovoid, egg-shaped, ellipsoidal, elliptical, etc. It may have pointed extremities, etc.

EXAMPLE

In one example application, a titanium twisted tube is to be inspected. The nominal dimensions of this example twisted tube are as follows. The tube ends have a circular cross-section with a 19.05 mm outside diameter and a 1.25 mm wall thickness. The twisted section of the tube has an elliptical shape with a major axis size of 22.23 mm and a minor axis size of 15.43 mm. The pitch of the helix in the twisted region of the tube is constant at 152.4 mm.

The example probe designed to inspect such a twisted tube includes a probe head which contains an elliptical shaped element and two outward biased protrusions linked by a neck portion. In this example, the two outward biased protrusions are two opposed flexible arms as shown in FIG. 4. The elliptical shaped element has its major axis at 15.3 mm, smaller than the circular diameter section of the twisted tube. The two flexible arms and the neck portion are made with Hydex™ stock shape plastics material manufactured by A.L. Hyde Company which is resilient enough to allow the arms to each be inwardly compressed by 2.9 mm allowing the major axis of the probe head to be reduced from 19.8 mm to 14.0 mm. The flexible arms are configured to be at an angle of 30° with respect to the main axis of the tube. The length of the each flexible arm (without the neck portion) is 19.75 mm which is about 6% of the helix pitch length. There are 4 eddy current sensors in the probe head, two bobbin coils located in the elliptical shape section and one pancake coil in the sensing section of each arm. The overall probe length is 185 mm.

The embodiments described above are intended to be exemplary only. The scope of the invention is therefore intended to be limited solely by the appended claims.

We claim:

1. An electromagnetic probe for non-destructive inspection of a twisted tube of a twisted tube heat exchanger, the twisted tube comprising at least one length of circular tube and a length of helical oval tube, said helical oval tube being an oval tube twisted into an helix, the probe comprising:
a probe body adapted to be inserted inside said twisted tube, said probe body having a sensing section provided at its distal end, said sensing section having at least one electromagnetic sensor connected to a respective at least one conductor provided within said probe body, said sensing section being configured to allow circulation of said probe body within said length of circular tube and said length of helical oval tube and to allow displacement of said at least one electromagnetic sensor from a radially inward contracted position to a radially outward expanded position in close proximity to an interior surface of a crest of said oval tube when said probe body is located in said length of helical oval tube, said close proximity being a distance smaller than a difference between a major axis and a minor axis of said helix;
a conduit attached to a proximal end of the probe body, said at least one conductor extending within said conduit to a remote end of said electromagnetic probe.

2. The electromagnetic probe as claimed in claim 1, wherein said sensing section comprises at least one outward biased protrusion biased to be in an expanded configuration, and being adapted to be movable to an inward contracted configuration upon external pressure from said interior surface of said twisted tube.

3. The electromagnetic probe as claimed in claim 2, wherein said at least one outward biased protrusion is two opposed outward biased protrusions.

4. The electromagnetic probe as claimed in claim 2, wherein each said at least one outward biased protrusion is one of a flexible arm, a compressible flange, a resilient flange, a spring-loaded flange and an outwardly biased flange.

5. The electromagnetic probe as claimed in claim 1, wherein said probe body has a probe head portion and a probe tail portion, said probe head and said probe tail portions being in rotational interconnection, said sensing section being provided on said probe head portion.

6. The electromagnetic probe as claimed in claim 5, further comprising at least one additional electromagnetic sensor on said probe tail portion of said probe body.

7. The electromagnetic probe as claimed in claim 5, wherein said rotational interconnection is a contact slip ring.

8. The electromagnetic probe as claimed in claim 5, wherein said probe tail portion has a circular cross section with a diameter maximized for displacement in said length of oval tube.

9. The electromagnetic probe as claimed in claim 1, further comprising at least one supplemental sensing section, said at least one supplemental sensing section being in at least one of rigid, angular and rotational interconnection with said sensing section, said supplemental sensing section having at least one supplemental electromagnetic sensor.

10. The electromagnetic probe as claimed in claim 9, wherein said supplemental sensing section is a helically shaped sensing section, a configuration of said helically shaped sensing section being adapted to match at least a portion of a pitch of said helix of said twisted tube.

11. The electromagnetic probe as claimed in claim 1, further comprising a spatial angular sensing device for determining an angular position of said at least one electromagnetic sensor in said twisted tube.

12. The electromagnetic probe as claimed in claim 1, wherein each said at least one electromagnetic sensor is chosen among the group consisting of a RFT emitter, a RFT receiver, an Eddy current emitter, an Eddy current receiver and an Eddy current combined emitter-receiver.

13. The electromagnetic probe as claimed in claim 1, wherein said electromagnetic sensor is one of a coil, a Hall effect sensor and a Giant Magneto-resistive sensor and if said electromagnetic sensor is a coil, said coil is one of a circular pancake coil, an oval pancake coil, a circumferential coil and an orthogonal coil.

14. The electromagnetic probe as claimed in claim 1, wherein said at least one electromagnetic sensor is an array of electromagnetic sensors.

* * * * *